(12) United States Patent
Hoffmann et al.

(10) Patent No.: US 7,988,643 B2
(45) Date of Patent: Aug. 2, 2011

(54) BIOPSY NEEDLE FOR THE HISTOLOGICAL EXAMINATION OF BODY TISSUE

(75) Inventors: Hans-Rainer Hoffmann, Neuwied (DE); Rudolf Matusch, Marburg (DE)

(73) Assignee: LTS Lohmann Therapie-Systeme AG (DE)

( * ) Notice: Subject to any disclaimer, the term of this patent is extended or adjusted under 35 U.S.C. 154(b) by 0 days.

(21) Appl. No.: 11/815,521

(22) PCT Filed: Jan. 19, 2006

(86) PCT No.: PCT/EP2006/000437
§ 371 (c)(1),
(2), (4) Date: Aug. 3, 2007

(87) PCT Pub. No.: WO2006/081947
PCT Pub. Date: Aug. 10, 2006

(65) Prior Publication Data
US 2008/0146964 A1     Jun. 19, 2008

(30) Foreign Application Priority Data

Feb. 3, 2005   (DE) .................. 10 2005 005 007

(51) Int. Cl.
*A61B 10/00*   (2006.01)

(52) U.S. Cl. ......... 600/567; 600/562; 600/563; 600/564
(58) Field of Classification Search .................. 600/562, 600/567, 563, 564
See application file for complete search history.

(56) References Cited

U.S. PATENT DOCUMENTS

| 4,403,617 | A | | 9/1983 | Tretinyak |
| 4,936,313 | A | * | 6/1990 | Burkhardt et al. ............ 600/564 |
| 5,018,530 | A | * | 5/1991 | Rank et al. .................... 600/562 |
| 5,197,482 | A | * | 3/1993 | Rank et al. .................... 600/562 |
| 5,257,632 | A | | 11/1993 | Turkel et al. |
| 5,303,718 | A | * | 4/1994 | Krajicek ....................... 128/897 |
| 5,333,619 | A | | 8/1994 | Burgio |
| 6,086,543 | A | * | 7/2000 | Anderson et al. ............ 600/567 |

(Continued)

FOREIGN PATENT DOCUMENTS

| DE | 88 07 566 U1 | 9/1988 |
| DE | 43 05 226 A1 | 9/1993 |
| DE | 298 23 300 U1 | 7/1999 |

(Continued)

OTHER PUBLICATIONS

Fuller Metric Parts Ltd, Screw Thread Conversion Table. (C) 1999-2008.<http://www.fullermetric.com/technical/information/tech_screw_thread_conversion.htm>.*

*Primary Examiner* — Max Hindenburg
*Assistant Examiner* — Sean P Dougherty
(74) *Attorney, Agent, or Firm* — Frommer Lawrence & Haug LLP

(57) ABSTRACT

The invention relates to a biopsy needle for obtaining material for histological examination of body tissue, in particular, of bone marrow, or for the isolation, culture and modification of body cells, comprising a cannula with a cutting edge and a manual turning handle and a stylet running in the cannula. At the end of the cannula is an internal thread and preferably an outer thread. An easily visible marking is preferably provided on the manual turning handle. On withdrawing the biopsy needle the biopsy sample is thus held in position in the cannula and the advancing is precisely controllable.

16 Claims, 1 Drawing Sheet

U.S. PATENT DOCUMENTS

| | | | |
|---|---|---|---|
| 6,110,128 A * | 8/2000 | Andelin et al. | 600/566 |
| 6,554,778 B1 * | 4/2003 | Fleming, III | 600/567 |
| 7,736,381 B2 * | 6/2010 | Biedermann et al. | 606/301 |
| 2004/0073139 A1* | 4/2004 | Hirsch et al. | 600/564 |
| 2005/0010215 A1* | 1/2005 | Delecrin et al. | 606/61 |

FOREIGN PATENT DOCUMENTS

| | | |
|---|---|---|
| DE | 200 10 879 U1 | 11/2000 |
| EP | 0 296 421 B1 | 4/1992 |
| EP | 0 738 126 B1 | 4/2002 |
| WO | WO 03/101306 A1 | 12/2003 |

* cited by examiner

BIOPSY NEEDLE FOR THE HISTOLOGICAL EXAMINATION OF BODY TISSUE

The invention relates to a biopsy needle for obtaining material for the histological examination of body tissue, in particular bone marrow, for the isolation, culture and modification of body cells, by introducing a biopsy needle into body tissue and removing the biopsy sample, and to a method and use thereof.

Bone biopsy instruments are sufficiently well known. The main parts are a cannula and a stylet which is guided in the latter and protrudes slightly from the open end of the cannula. The cannula end is likewise provided with a cutting edge. The other end of the cannula has a handle that ensures secure guiding of the biopsy needle. With the stylet inserted into it, the biopsy needle is easily introduced percutaneously as far as the bone. After the stylet has been removed, the cannula has to be axially driven further into the body tissue, in particular into the cortical or compact substance. In some cases, a biopsy hammer is also used for this purpose.

As the cannula is forced in and at the same time turned about its axis, the end of the cannula cuts out a cylindrical sample from the tissue, which sample is received in the interior of the cannula.

To achieve separation of the biopsy sample from the surrounding material, the cannula is in most cases subjected to tilting movements or vibrations. This often causes small fractures on the surface and breaks in the hard tissue into which the cannula has been driven. The consequence of this is pain and trauma to the patient and damage to the biopsy needle which, by bending, has lost the required rectilinear shape. Nevertheless, the biopsy material often does not remain in the cannula, and instead it slips partially or completely out of the end of the cannula. This is caused by incomplete separation from the rest of the tissue and, in addition, by an underpressure, albeit only a slight one, between the specimen inside the cannula and the puncture channel created by the withdrawal of the biopsy needle from the tissue. If the specimen partially protrudes from the cannula, it may also be scraped off by the skin, which acts like an elastic rubber membrane, and can thus remain in the body. All of this makes it necessary to repeat the entire biopsy examination and places a burden on the patient and the treating physician.

Different approaches to solving this problem are to be found in the prior art.

G 88 07 566 describes a biopsy needle in which the distal end of the cannula is roughened like a rasp or is provided with a thread in order to facilitate penetration into the bone by turning. The removal of the sample is assisted by the fact that an underpressure is created in the cannula by means of a suction syringe applied to the cannula.

DE 43 05 226 discloses an auxiliary device for biopsy needles, which auxiliary device is composed of a structure that can be inserted at the proximal end and slides between the inside wall of the cannula and the cylinder of tissue. The biopsy sample is squeezed together in this way. A disadvantage is that this procedure can lead to compression artefacts and to inaccurate examination results.

DE 298 23 300 U1 discloses, in one embodiment, a biopsy needle with a cylindrical outer thread at the distal end of the cannula, with a safety groove present in the interior of the cannula before the distal end. The internal diameter of the cannula thus decreases from the safety groove to the distal end of the cannula and is intended to serve as a resistance during withdrawal. A disadvantage of this design is that the sample has to be ejected via the proximal end of the cannula, and the sample is damaged or even destroyed by the sliding from the distal end of the cannula.

EP 0 738 126 B1 discloses a biopsy needle composed of an outer cannula, of an inner tube and of a sleeve, the distal end of the inner tube being provided with a coil in the shape of a loop which extends inside the inner tube, and the free end of the loop is secured on the inner surface of the outer cannula. When the inner tube is turned relative to the outer cannula, the loop reduces its diameter, in order to release or hold the biopsy sample inside the outer needle. A disadvantage is the fairly complicated and therefore expensive production process.

DE 200 10 879 U1 discloses a biopsy needle with removal system, wherein the removal system can be pushed into the cannula. The front end is sleeve-shaped and, in order to receive the sample, is slit, such that two retaining parts are formed. A disadvantage of this system is the possible damage to the sample material as a result of the sample being clamped for removal from the cannula.

The object of the present invention was to make available a biopsy needle which is suitable for the histological examination of solid body tissue, which permits a biopsy examination that is easier to perform and places less burden on the patient, and which at the same time overcomes the disadvantages of the systems described in the prior art.

The object is achieved surprisingly simply by the biopsy needle disclosed in claim 1 and by the preferred embodiments specified in the dependent claims. The invention not only affords greater reliability of sample collection compared to articles in the prior art, but at the same time represents a simple and inexpensive solution, in particular since the patient is assured to a greater extent by the demonstrably more reliable conduct of the biopsies.

The biopsy needle disclosed in claim 1 is used for obtaining material for the histological examination of solid to fatty body tissue, in particular bone marrow. It is composed of a cannula with manual turning handle, which cannula is provided at its end with a cutting edge, and of a stylet guided in the cannula. There is an inner thread at the end of the cannula.

The dimensions of the biopsy needle according to the invention usually involve an overall length of 150 mm, preferably 140 mm, length of free extension area less than 100 mm, external diameter less than 5 mm, preferably 3-4 mm, internal diameter 1.5 to 2.5 mm, wall thickness in thread area 0.5 to 0.8 mm.

After the biopsy needle, as described at the outset, has been inserted percutaneously and has been introduced far enough into the sample material, the biopsy needle is withdrawn together with the biopsy sample located in the cannula. In this step, the biopsy sample is separated from the rest of the tissue. By virtue of the inner thread located at the end of the cannula, the biopsy sample now has good contact via the thread with the cannula and is held in position. The forces that hold the sample in the interior of the cannula are now greater than the forces of separation on the tissue. It can now be completely removed.

By means of an underpressure in the cannula, for example an underpressure created by a suction syringe, it is possible to additionally secure the biopsy sample against slipping out of place. Circular gyratory movements of the cannula for separating the sample material from the rest of the tissue are therefore superfluous. This means a considerable reduction of possible trauma to the patient.

The sample is now easily and safely removed in reverse sequence through the end of the cannula of the biopsy needle. To do this, the stylet is inserted from the handle end of the biopsy needle into the cannula and, by being turned counter to the direction of rotation of the inner thread, releases the biopsy sample smoothly from the preferably cylindrical cannula.

However, the cannula can also preferably be shaped conically in the front area, such that only a small part of the sample is in contact with the thread, and, consequently, the sample material is affected to the least possible extent.

In a particularly preferred embodiment, a further thread is additionally arranged on the outside of the end of the cannula in order to ensure better guiding during insertion into solid body tissue, in particular bone, and to avoid the risk of tilting. The inner and outer threads have the same pitch and are ideally matched to one another. The inner and outer threads are preferably cut or rolled such that the maximum wall thickness or the cannula in the area of the threads remains constant, or such that the difference in the minimum and maximum wall thickness is as small as possible. In this embodiment of the biopsy needle, the external diameter of the outer thread does not exceed the outer circumference of the cannula. The cannula is thus reliably guided axially by the outer thread and turns with self-tapping into the bone material.

The biopsy needle with the sample is easily withdrawn (without turning) from the tissue (possibly with the assistance of an underpressure). The outer thread is advantageously overground or rolled, i.e. no burrs are present. This ensures that muscle substance and tissue do not become wound up on the thread during insertion, and it also prevents splintering of the bones during removal.

The effectiveness of the article according to the invention is clearly demonstrated by the much smaller number of unsuccessful attempts in the example set out below.

The thread(s) has (have) a single or multiple helix or a double helix and is (are) preferably overground or rolled as right-hand thread or left-hand thread. Suitable threads are in inches or freely selected, particularly suitable are metric threads. The thread pitch is advantageously 1 mm for thread dimensions outer M4×1 and inner M3×1 or 0.5, outer M4×0.5 and inner M3×0.5, or outer M3×0.5 and inner M2×0.5.

To be able to precisely control and determine the advance of the cannula into the bone material, an easily visible marking is provided on one side of the manual turning handle. For example, for the thread dimensions outer M4×1 and inner M3×1, this means that, upon a complete revolution of the biopsy needle, the cannula moves 1 mm deeper into the examination material; for thread dimensions outer M4×0.5 and inner M3×0.5 or outer M3×0.5 and inner M2×0.5, the biopsy needle moves 0.5 mm deeper into the examination material. The person performing the biopsy is thus able to precisely control the exact depth of insertion into the bone material and to ensure a smooth insertion and extraction of the biopsy needle.

The cutting edge at the end of the cannula can be beveled. The shape of the cutting edge can preferably be wave-shaped or crown-shaped. By means of this saw-type cutting, effected by the rotation movement of the biopsy needle, the insertion into the bone material, e.g. the cortical lamina, is made easier.

The material of the biopsy needle is metal, preferably stainless steel, in order to ensure the required stability. However, paramagnetic materials, preferably titanium, nickel/titanium or carbon, are also advantageous if tests are carried out at the same time by means of magnetic resonance tomography.

The stylet guided in the cannula is preferably connected to the manual turning handle via a Luer lock adapter in order to ensure a secure fit in the biopsy needle. It preferably has a wedge-shaped ground surface at the tip, similar to a screwdriver, or a trocar ground surface. Since, as has already been mentioned, it protrudes past the cannula end, the biopsy needle can be inserted easily into the tissue. After contact with the bone surface, the uppermost hard layer is ablated by turning. The stylet is then removed, and the biopsy is performed by turning the cannula. At the same time, the stylet serves most effectively for removal of the biopsy sample. To do this, the stylet is introduced from the direction of the handle of the biopsy needle into the cannula and, by means of turning counter to the direction of rotation of the inner thread, easily removes the biopsy sample, similar to the function of a screwdriver.

Figure 1:
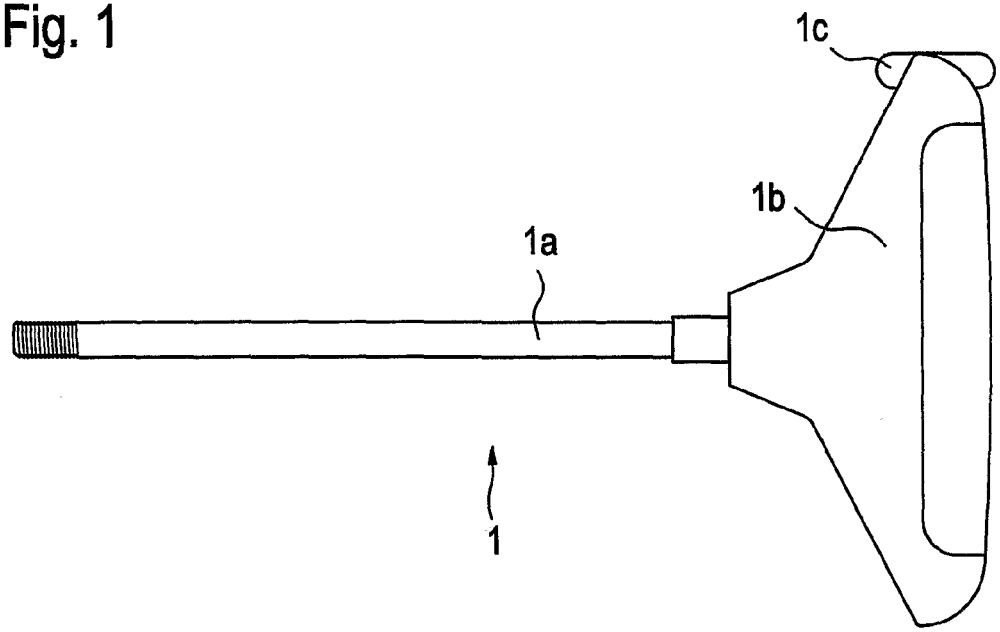
FIG. 1 shows a biopsy needle (1) composed of a cannula (1a), an outer thread and an inner thread (not shown) located at its end, a manual turning handle (1b) with marking (1c).
Figure 2:
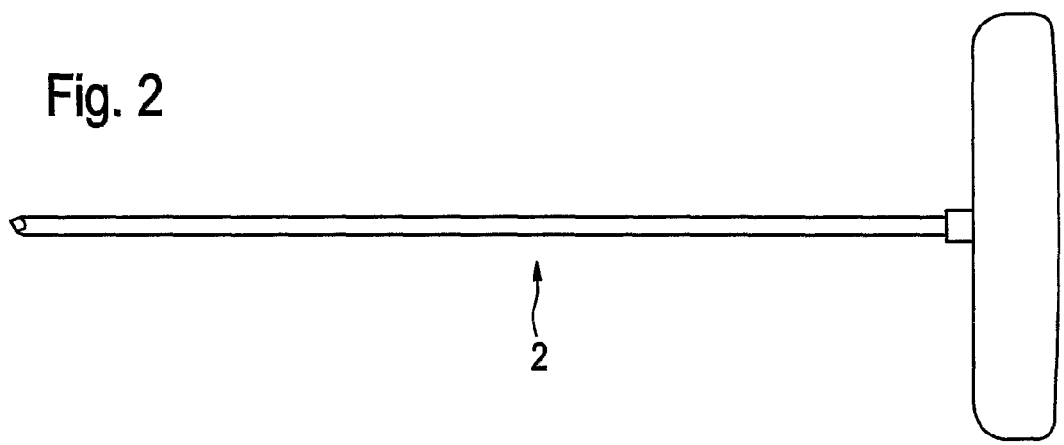
FIG. 2 shows a stylet (2) matching the biopsy needle, with a wedge-shaped ground surface at the end of the stylet.
Figure 3A:
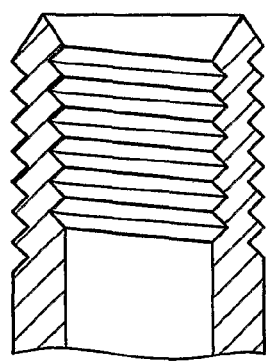
Figure 3B:
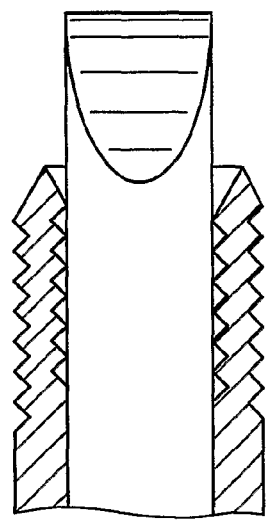

FIG. 3a shows, in a view sectioned in the longitudinal direction, the end of the cannula (1a) of the biopsy needle in a preferred embodiment of the invention. It shows the overground or rolled inner and outer threads and a cutting edge located at the end of the cannula. FIG. 3b shows the stylet (2) already introduced into the cannula.

To obtain material for the histological examination of body tissue, the biopsy needle according to the invention, with inserted stylet, is easily introduced percutaneously as far as the examination material, preferably bone material.

After contact with the bone surface, the uppermost hard layer is ablated by turning the wedge-shaped ground surface of the stylet. The stylet is then removed, and the biopsy is performed by turning the cannula. As the cannula is forced in and turned at the same time about its axis, the biopsy needle cuts into the examination material with the aid of the cutting edge, in particular assisted by an outer thread at the end of the cannula in a preferred embodiment. The check on whether there is sufficient sample material in the cannula is based on the number of rotations of the biopsy needle, the sample being taken up in the interior of the cannula. The biopsy needle with the examination sample is then withdrawn and the sample material, preferably in reverse order, is screwed out from the end of the cannula with the aid of the stylet.

Two sets of 20 bone marrow biopsies were performed, with the thread dimensions of the cannula being outer M4×0.5 mm and inner M3×0.5.

| Cannula type | With inner and outer threads | With no thread | Chi-square test for unconnected random samples |
|---|---|---|---|
| Biopsy failure | 1 | 8 | p = 0.0080 |
| Success | 19 | 12 | |
| Total | 20 | 20 | |

The invention claimed is:
1. A biopsy needle for obtaining material for histological examination of body tissue, composed of a cannula with a manual turning handle and of a stylet guided in the cannula, the cannula being provided with a shaped cutting edge at a cannula end,
characterized in
that the cannula end additionally has an area of threads including an inner thread arranged on an inside of the cannula end and an outer thread arranged on an outside of the cannula end, that the inner and outer threads have a pitch and the pitch of the inner and outer threads are matched, that the area of the threads has a wall thickness, wherein the wall thickness is constant, that the cannula has an outer circumference and the outer thread has an externa diameter where the external diameter of the outer thread does not exceed the outer circumference of the cannula, and that the cannula has an inner circumference and the inner thread has an internal diameter where the internal diameter of the inner thread does not exceed the inner circumference of the cannula.

2. The biopsy needle as claimed in claim 1 characterized in that the threads have a single helix, a multiple helix or a double helix.

3. The biopsy needle as claimed in claim 1 characterized in that the inner and outer thread is a metric ISO thread.

4. The biopsy needle as claimed in claim 3, characterized in that the inner and outer threads have dimensions of outer M4×1 and inner M3×1, outer M4×0.5 and inner M3×0.5, or outer M3×0.5 and inner M2×0.5.

5. The biopsy needle as claimed in claim 1 characterized in that the cannula is shaped conically in a front area of the cannula.

6. The biopsy needle as claimed in claim 1 characterized in that the end of the cannula is beveled.

7. The biopsy needle as claimed in claim 1 characterized in that the cutting edge of the cannula has a wave-shaped ground surface.

8. The biopsy needle as claimed in claim 1 characterized in that the cannula is made of metal, or of a material compatible with magnetic resonance.

9. The biopsy needle as claimed in claim 1 characterized in that the stylet guided in the cannula has a trocar ground surface or a wedge-shaped ground surface at a tip of the needle.

10. The biopsy needle as claimed in claim 1 characterized in that the manual turning handle is provided with a marking for controlled advance.

11. A method for obtaining sample material for histological examination of body tissue, characterized in that a biopsy needle as claimed in claim 1, with inserted stylet, is introduced percutaneously into an area for examination, the stylet is removed after a few rotations of the stylet, the biopsy needle is inserted by rotary movement sufficiently far into the area for examination, the biopsy needle with the sample material is withdrawn, and the sample material is removed from the cannula.

12. A method for obtaining material for histological examination of body tissue or for isolation, culture and modification of body cells which comprises inserting the biopsy needle of claim 1 into the body tissue.

13. The biopsy needle of claim 1, wherein the body tissue is bone marrow.

14. The biopsy needle of claim 2, wherein the threads are overground or rolled.

15. The biopsy needle of claim 8, wherein the cannula is made of metal.

16. The biopsy needle of claim 8, wherein the cannula is made of titanium, nickel/titanium or carbon.

* * * * *